United States Patent
Dominguez

(10) Patent No.: US 6,740,055 B2
(45) Date of Patent: May 25, 2004

(54) TRAUMA CERVICAL COLLAR

(76) Inventor: Steven Dominguez, 19 Bridington, Laguna Niguel, CA (US) 92677

( * ) Notice: Subject to any disclaimer, the term of this patent is extended or adjusted under 35 U.S.C. 154(b) by 190 days.

(21) Appl. No.: 09/956,366

(22) Filed: Sep. 18, 2001

(65) Prior Publication Data

US 2003/0055367 A1 Mar. 20, 2003

(51) Int. Cl.[7] .................................................. A61F 5/00
(52) U.S. Cl. ......................................................... 602/18
(58) Field of Search ................................ 602/17–18, 4, 602/36, 32, 38; 128/DIG. 23, 97.1

(56) References Cited

U.S. PATENT DOCUMENTS

| | | | | | |
|---|---|---|---|---|---|
| 1,803,556 A | * | 5/1931 | Nugent | ......................... | 602/19 |
| 3,313,297 A | * | 4/1967 | Applegate et al. | ............ | 602/18 |
| 3,507,273 A | * | 4/1970 | Yellin | ........................... | 602/18 |
| 3,601,123 A | * | 8/1971 | McFarland | ................... | 602/18 |
| 3,605,736 A | * | 9/1971 | D'amico et al. | .............. | 602/36 |
| 3,776,224 A | * | 12/1973 | McFarland | ................... | 602/18 |
| 4,141,368 A | * | 2/1979 | Meyer | .......................... | 602/18 |
| 4,194,501 A | * | 3/1980 | Watt | ............................. | 602/36 |
| 4,383,523 A | * | 5/1983 | Schurman | .................... | 602/36 |
| 4,628,913 A | * | 12/1986 | Lerman | ........................ | 602/18 |
| 5,016,623 A | * | 5/1991 | Krahenbuhl | ................. | 602/27 |
| 5,054,475 A | * | 10/1991 | Calabrese et al. | ............. | 602/17 |
| 5,385,535 A | * | 1/1995 | McGuinness | ................ | 602/18 |
| 5,409,450 A | * | 4/1995 | Donelson | ..................... | 602/18 |
| 5,433,696 A | * | 7/1995 | Osti | ............................. | 602/18 |
| 5,520,619 A | * | 5/1996 | Martin | ........................... | 602/5 |
| 5,575,763 A | * | 11/1996 | Nagata et al. | ................. | 602/18 |
| 5,964,722 A | * | 10/1999 | Goralnik et al. | .............. | 602/18 |
| 6,210,354 B1 | * | 4/2001 | Ousdal | ......................... | 602/36 |

* cited by examiner

*Primary Examiner*—Nicholas D. Lucchesi
*Assistant Examiner*—Huong Q. Pham

(57) ABSTRACT

An improved trauma cervical collar for supporting a patient's neck that is adjustable to the patient's neck size in the anterior to posterior and medial to lateral and cephalad to caudal planes. The collar includes a pair of semi-elliptical shaped side members. Each side member includes buckles for attaching securing straps. An occipital securing strap supports the back of the patient's head and has two ends for attachment to the buckles, one on each of the side members. A back rest securing strap has two ends for attachment to the buckles, one on each of the side members. A mandible securing strap for support of the patient's chin has two ends for attachment to the buckles, one on each of the side members. A chest securing strap has two ends for attachment to the buckles, one on each of the side members. The buckles are spring-loaded to quickly attach to and hold the straps at various lengths as required.

16 Claims, 5 Drawing Sheets

TRAUMA CERVICAL COLLAR

BACKGROUND OF THE INVENTION

1. Field of the Invention

The present invention relates generally to a cervical collar and in particular to an improved multi-size cervical collar that is easy to use by pre-hospital personnel in the field.

2. Description of Related Art

Currently there are multitudes of "fixed" trauma cervical collars that require manipulation of the collar or the patient. There are several manufacturers of "adjustable" trauma cervical collars, all utilizing the same rigid technology that only allows for front-to-back adjustments via such fasteners as Velcro tape. The rigidity and instability to adjust to an individual patient's neck size provides a poor form and fit. This is especially crucial in a highly traumatized or a head-injured patient who has a higher probability of cervical neck injury or fracture. Obviously, any manipulation of the patient's neck is to be avoided in trauma; however, the reality is that this does exist to some degree. Cost-containment methods require the pre-hospital ambulance services to purchase and use a limited number of size-appropriate cervical collars. The incidence of trauma patient cervical spine manipulation is increasing, which inherently increases the risk of adverse patient outcomes and malpractice suits.

Cervical collars have been used by physicians and emergency medical technicians for a number of years. Such devices provide initial support of the head in a neutral position. The fundamental task of a cervical collar is to geometrically constrain the wearer's head relative to her neck and back to minimize further (and possibly damaging) movement. In order to meet this goal, the collar must be sized so as to accommodate the geometrical parameters presented by the wearer, such as the circumference of her neck and her neck length—the distance between the wearer's mandible and the top of the wearer's shoulder (at the trapezius muscle). If the collar is not properly fitted to the wearer, the wearer's head may not be supported in a neutral position with the proper degree of support against unwanted movement.

Variations of neck circumference can be dealt with in an economical manner by various systems now on the market, such as that disclosed in U.S. Pat. No. 5,520,619. A primary problem with this prior art collar is that the physician may not be able to examine the back of the neck to determine the extent of neck injury without removal of the collar.

Therefore, a need exists for a single cervical collar that can accommodate a variety of sizes of patients, including variation in neck length, so as to minimize the storage and transport space requirements. Moreover, it would be helpful if the collar could allow a complete examination by a physician without removing the collar.

OBJECTS AND SUMMARY OF THE INVENTION

It is accordingly an object of the present invention to provide an expandable trauma cervical collar that automatically adjusts to the patient's neck size in the anterior to posterior and medial to lateral and cephalad to caudal planes.

Another object of the present invention is to provide a trauma cervical collar that is a custom fit to the patient and securely immobilizes and stabilizes the patient's neck, thereby reducing the risk of injury during transport of the patient with a potentially fractured neck.

Still another object of the present invention is to provide a collar constructed of a plastic polymer, thereby providing a rigid, stable environment for the protection of potentially serious cervical neck injuries.

Yet another object of the present invention is to provide a cervical collar that is fully adjustable in length, width, and height making it unnecessary for pre-hospital personnel to carry up to 15 different sizes of collars.

Still yet another object of the present invention is to provide a cervical collar that utilizes a totally new "expandable" design that completely eliminates cervical movement during transport of the patient.

Another object of the present invention is to provide a cervical collar that does not need to be removed to conduct an examination of the patient's neck either anteriorly or posteriorly, allowing examination of the posterior cervical spine and anterior neck structures such as the larynx and great vessels without removal of the cervical collar.

These and other objects, which will become apparent as the invention is described in detail below, are provided by an improved trauma cervical collar for supporting a patient's neck that automatically adjusts to the patient's neck size in the anterior to posterior and medial to lateral and cephalad to caudal planes. The collar includes a pair of semi-elliptical or ovoid shaped side members wherein each side member includes buckles for attaching a plurality of securing straps. An occipital securing strap supports the back of the patient's head and has two identical ends for attachment to the buckles on each of the side members. A back rest securing strap has two identical ends for attachment to the buckles on each of the side members. A mandible securing strap for support of the patient's chin has two identical ends for attachment to the buckles on each of the side members. A chest securing strap has two identical ends for attachment to the buckles on each of the side members.

BRIEF DESCRIPTION OF THE DRAWINGS

The general purpose of this invention, as well as a preferred mode of use, its objects and advantages will best be understood by reference to the following detailed description of an illustrative embodiment with reference to the accompanying drawings in which like reference numerals designate like parts throughout the figures thereof, and wherein.

DETAILED DESCRIPTION OF THE PREFERRED EMBODIMENTS

Figure 1:
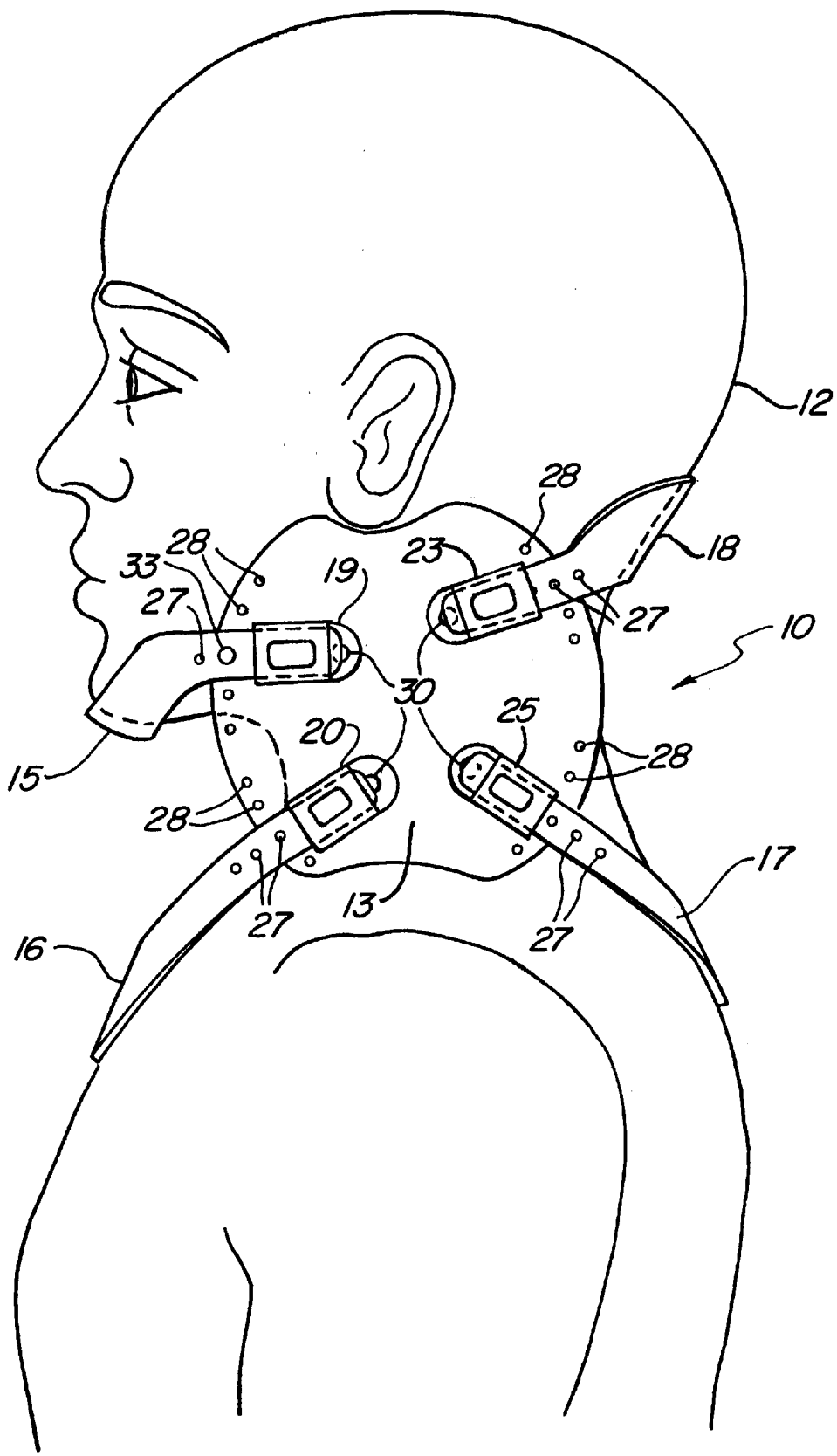
FIG. 1 illustrates a perspective view of the trauma cervical collar according to the present invention on a patient.

Referring now to the drawings and FIG. 1 in particular, a perspective view of a trauma cervical collar 10 fitted on a patient 12 and constructed in accordance with the teachings of the present invention is shown. A pair of identical side members 13 and 14 (FIG. 2) are placed on either side of the patient's head and secured to one another by a mandible strap 15, a chest strap 16, a back rest strap 17, and an occipital strap 18. As will be shown in greater detail hereinbelow, the straps 15 to 18 are pivotally mounted to the side members 13 and 14. Each of the straps 15 to 18 are also adjustable in length in order to fit the collar 10 to a large number of different sized patients. The side members 13 and 14 are preferably ovoid with the ends of the oblong shape being truncated to fit under the ear and on the shoulder of the wearer as shown in FIG. 1.

The straps 15, 16, 17, and 18 are rotatable about a pivot point within their respective buckles 19, 20, 21, 22, 23, 24, 25, and 26. Each of the buckles 19 to 26 receive ends of their respective straps 15 to 18. Each strap 15 to 18 includes openings 27 for receiving a stud 28, 30, which holds the strap at a desired angle. The openings 27 are placed along the length of each strap in an area near the edge of the side members 13 and 14. The studs 28 are located along the periphery of each side member 13 and 14 in an area near where the straps cross the edge of the side member.

Figure 2:
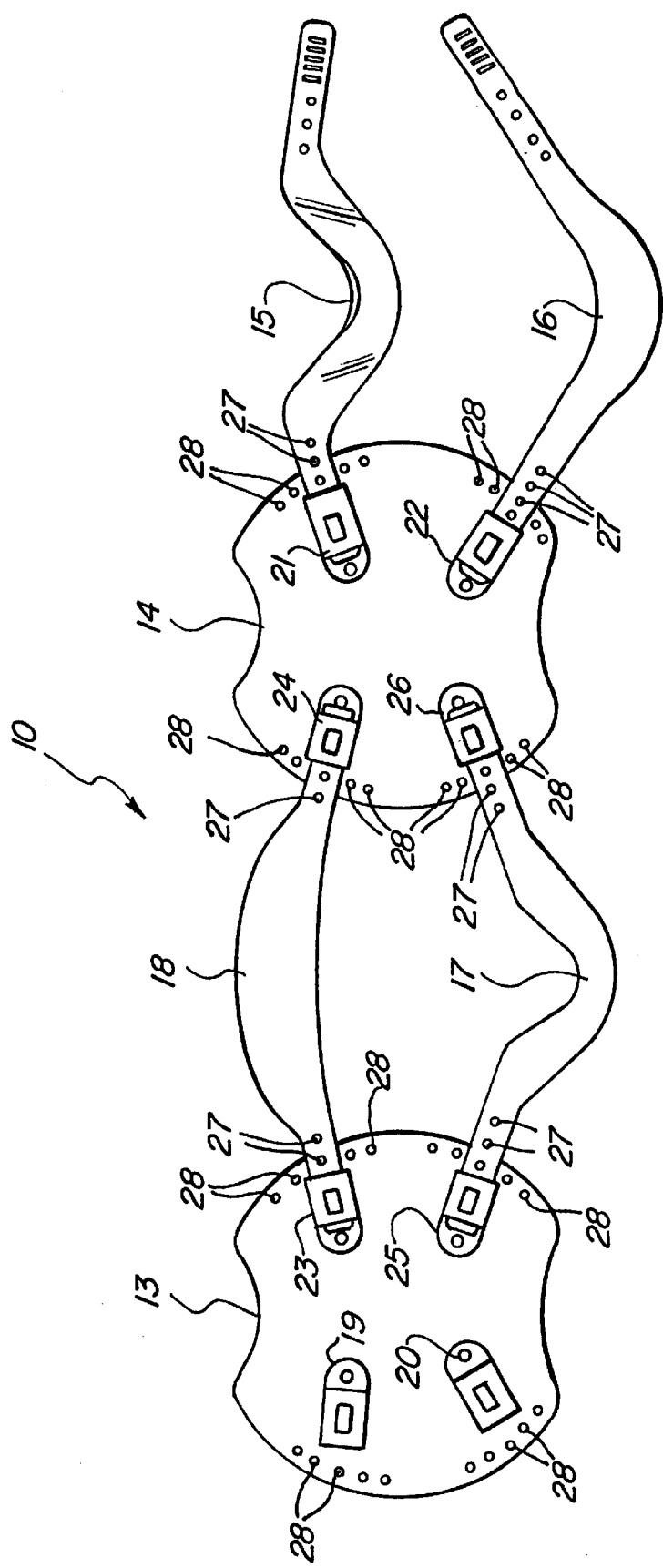
FIG. 2 is a side view of the collar of FIG. 1 when extended in a flat position.

Referring now to FIG. 2, a view of the collar 10 is shown extended out in a flat position. Each of the side members 13 and 14 are identical in shape. Each side member is formed of a hard, yet flexible plastic. The straps 17 and 18 connect the two side members together, but are adjustable as will be explained below. The straps 15 and 16 are pivotally mounted to the side member 14 by means of buckles 21 and 22, respectively. The straps 17 and 18 are pivotally mounted to the side member 13 by buckles 23 and 25, respectively. The straps 17 and 18 are pivotally mounted to the side member 14 by the buckles 24 and 26, respectively. The straps 15 and 16 are wrapped around the front of a patient (as shown in FIG. 1) and then pivotally fastened to buckles 19 and 20, respectively.

Figure 3:
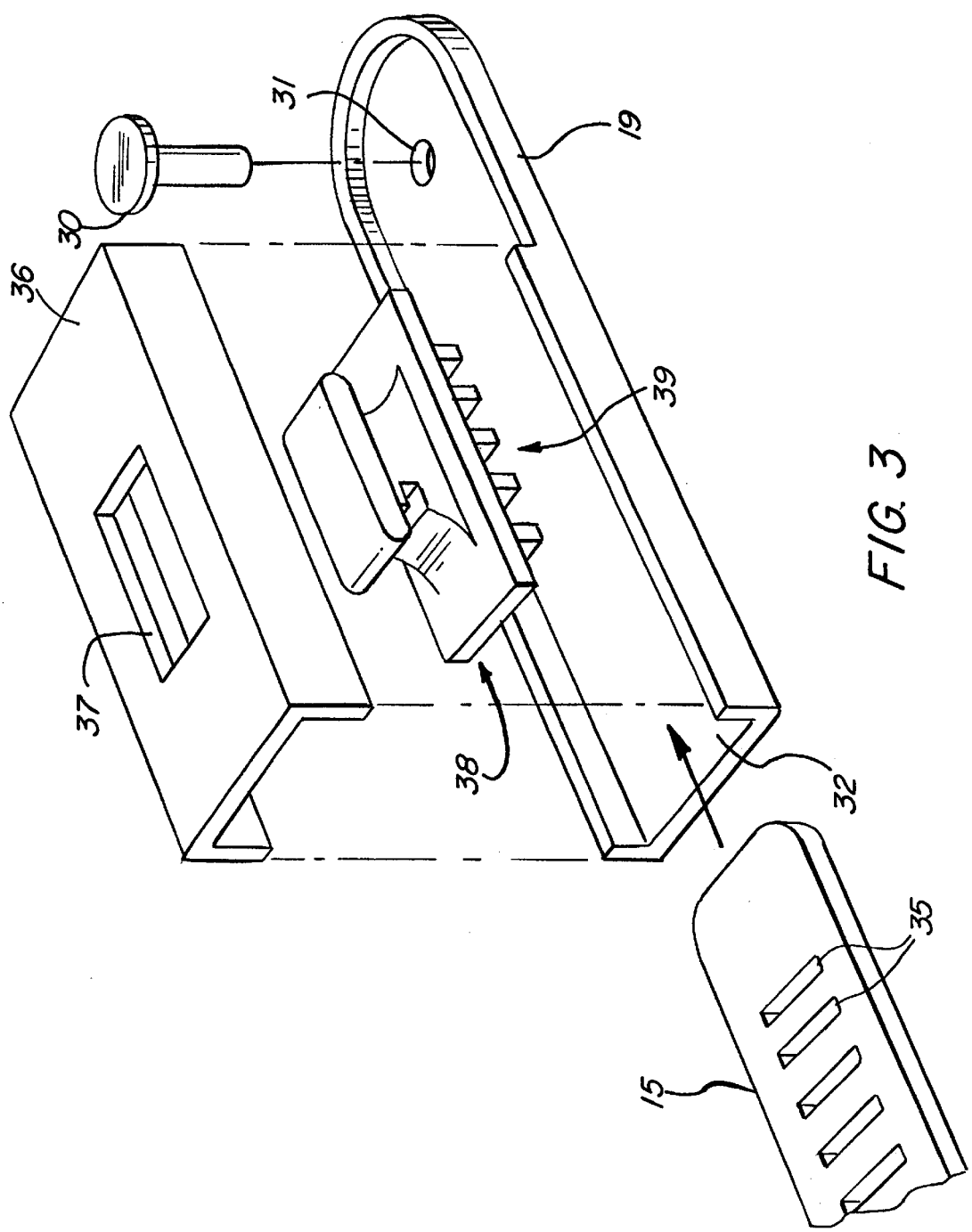
FIG. 3 is a perspective-exploded, assembly view of a strap guide for use with the collar of the present invention.

Details of the buckles 19, 20, 21, 22, 23, 24, 25, and 26 are shown in FIG. 3. Each buckle is pivotally anchored to a side member (13 or 14) by means of a pin 30 that fits through an opening 31 in the buckle 19 and an opening in a side member (not shown). A channel 32 is formed in the buckle for receiving an end of a strap 15. The end of the strap 15, which is shown in partial view, includes a series of slots 35. The channel 32 is covered, in part, by a cap 36 having a center slot 37 formed therein. A grip 38 having a series of teeth 39 sized to engage the slots 35 of the strap 15, fits with the slot 37.

Figure 4A:
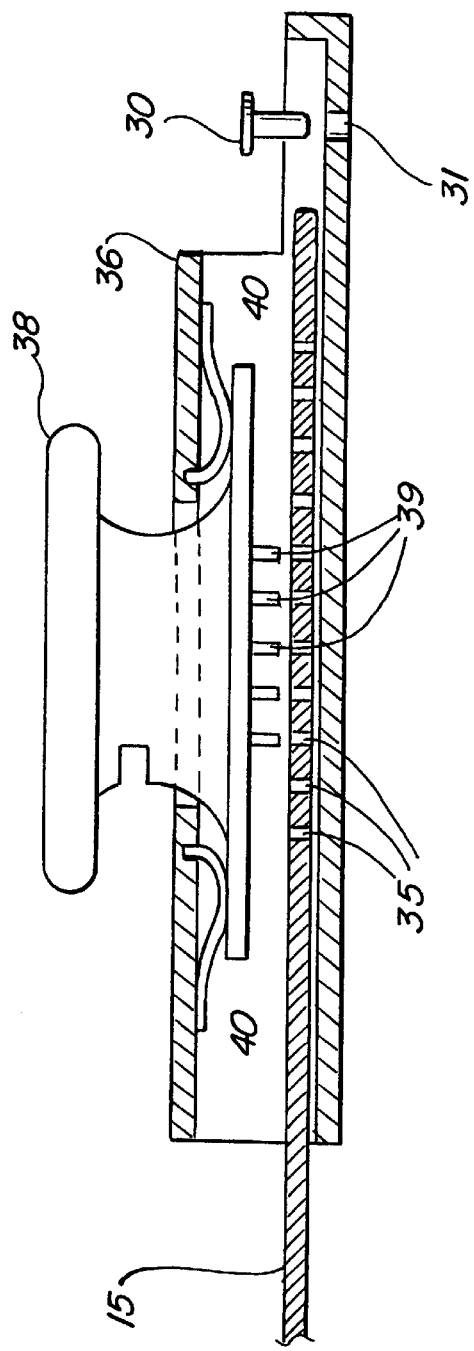
FIGS. 4A and 4B are cross-sectional views of the strap guide showing how it fastens a strap.
Figure 4B:
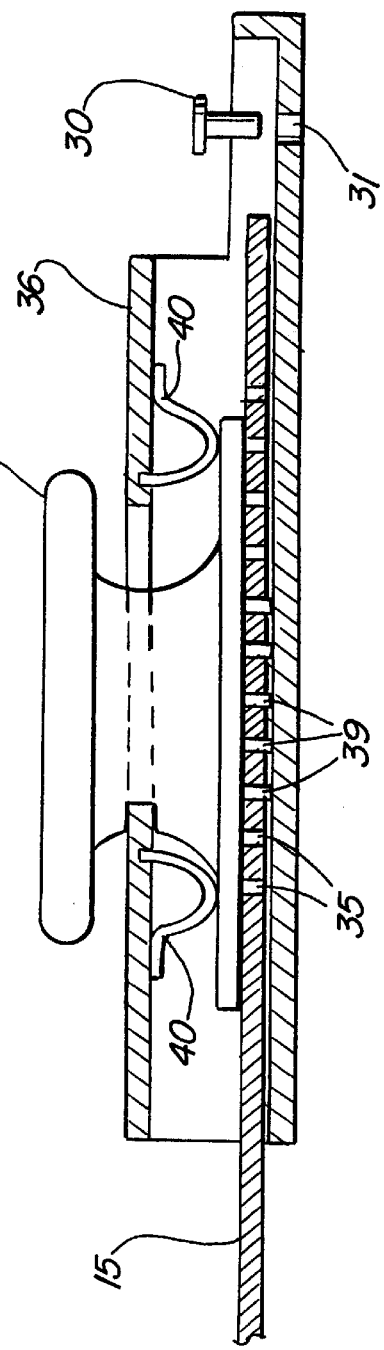

FIGS. 4A and 4B are cross-sectional views of the buckle shown in FIG. 3, wherein like reference numerals identify like components of the buckle. In FIG. 4A, the grip 38 is manually lifted, against the bias of springs 40, and moved into place for the teeth 39 to engage the slots 35 in the strap 15. Once the grip is released it is moved downward by the force of the springs 40 so that the teeth 39 firmly engage the strap 15, locking the strap in place.

Referring to FIG. 1, the opening 27 in the strap 15 carries a stud 33 that slides into an opening 28 in the side member to lock the strap into a desired angle with the side member 13. Thus, the strap 15 is locked at a preferred angle by the buckle 19 at one end thereof and by the stud 33 engaging an opening 27 along the length of the strap and an opening 28 in the side member. The other end of strap 15 is similarly fastened. Each of the other straps 16, 17, and 18 are adjusted in the same manner, thereby providing a custom fit for the patient 12.

Figure 5:
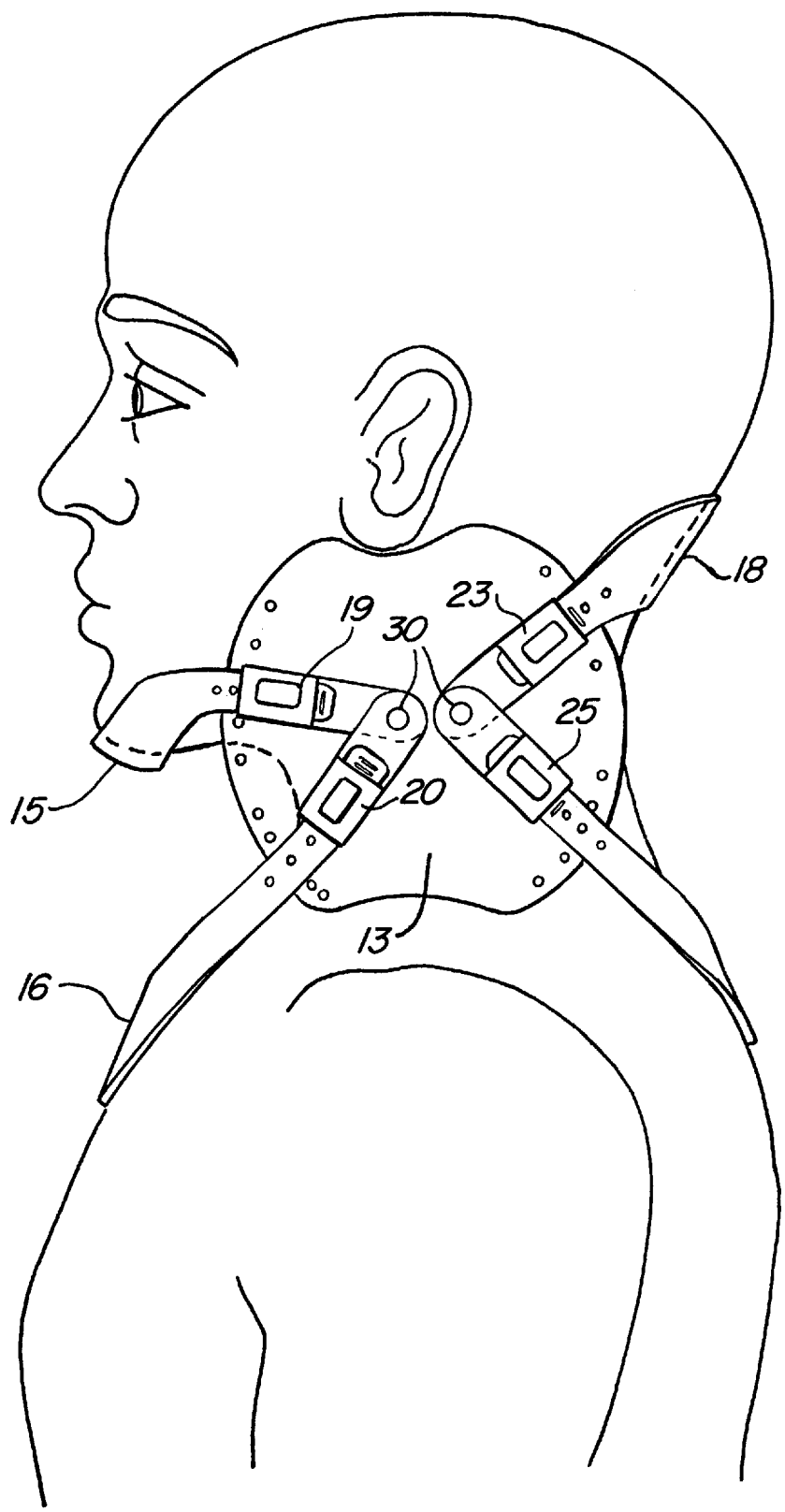
FIG. 5 is a perspective view of the trauma cervical collar according to the present invention in an alternate embodiment.

FIG. 5 illustrates an alternate embodiment wherein a pair of buckles 19, 20 and 23, 25 are pivotally anchored to side member 13 by a single pin 30.

While the invention has been particularly shown and described with reference to a preferred embodiment, it will be understood by those skilled in the art that various changes in form and detail may be made therein without departing from the spirit and scope of the invention.

What is claimed is:

1. A trauma cervical collar for a human patient comprising:
   two side members with a predetermined periphery located between the ear and shoulder of the patient;
   an occipital strap having two ends, each end adapted for attachment to one of said side members;
   a back rest strap having two ends, each end adapted for attachment to one of said side members;
   a mandible strap having two ends, each end adapted for attachment to one of said side members;
   a chest strap having two ends, each end adapted for attachment to one of said side members; and
   a plurality of buckles mounted to said side members, the strap ends fitting into respective buckles.

2. The collar of claim 1 further comprising a pivotal pin mounting each of the buckles to a side member.

3. The collar of claim 1 wherein each of the side members includes studs mounted along a portion of the periphery.

4. The collar of claim 1 wherein each of said side members includes studs mounted along a portion of the periphery and each of said straps includes holes formed therein for receiving one of the studs, whereby each strap may be set at a desired angle with respect to a side member.

5. The collar of claim 1 wherein said side members are ovoid in shape.

6. The collar of claim 1 wherein said buckles are pivotally mounted onto said side members.

7. The collar of claim 1 wherein each of said buckles include a grip having teeth for engaging slots in a strap so as to lock the strap into a fixed position.

8. A trauma cervical collar for supporting a patient's neck comprising:
   a pair of side members having a predetermined periphery;
   a plurality of buckles mounted on each side member;
   an occipital strap for supporting the back of a patient's head having two ends for attachment to two buckles, one on each of the side members;
   a back rest strap having two ends for attachment to two buckles, one on each of the side members;
   a mandible strap for supporting a patient's chin having two ends for attachment to two buckles, one on each of the side members; and,
   a chest strap having two ends for attachment to two buckles, one on each of the side members.

9. The collar of claim 8 wherein the buckles are pivotally mounted to the side members.

10. The collar of claim 8 further comprising side studs mounted along the periphery of each of the two side members.

11. The collar of claim 8 further comprising studs mounted along the periphery of each of the side members and each of the straps includes holes for receiving one of said studs; whereby the straps may be set at a desired angle with respect to the side members.

12. The collar of claim 8 wherein each of said buckles include a grip having teeth for engaging slots in a strap so as to lock the strap into a fixed position.

13. An improved trauma cervical collar for supporting a patient's neck that is adjustable to the patient's neck size in the anterior to posterior and medial to lateral and cephalad to caudal planes, said collar comprising:

a pair of shaped side members;

a plurality of buckles attached to each one of the side members;

an occipital securing strap for supporting the back of the patient's head having two ends for attachment to the buckles, on each of the side members;

a back rest securing strap having two ends for attachment to the buckles, on each of the side members;

a mandible securing strap for supporting the patient's chin and having two ends for attachment to the buckles, on each of the side members; and, a chest securing strap having two ends for attachment to the buckles, on each of the side members.

14. The collar of claim 13 wherein each of the buckles is pivotally mounted to a side member.

15. The collar of claim 13 further comprising studs mounted along the periphery of each of the side members and each of the straps including holes for receiving one of the studs; whereby the straps may be set at a desired angle with respect to a side member.

16. The collar of claim 13 wherein each of said buckles include a grip having teeth for engaging slots in a strap so as to lock the strap into a fixed position.

* * * * *